United States Patent [19]

Mitchell

[11] Patent Number: 5,521,703

[45] Date of Patent: May 28, 1996

[54] DIODE LASER PUMPED RAMAN GAS ANALYSIS SYSTEM WITH REFLECTIVE HOLLOW TUBE GAS CELL

[75] Inventor: John R. Mitchell, Salt Lake City, Utah

[73] Assignee: Albion Instruments, Inc., Salt Lake City, Utah

[21] Appl. No.: 323,785

[22] Filed: Oct. 17, 1994

[51] Int. Cl.⁶ .................................................. G01J 3/44
[52] U.S. Cl. ............................................................ 356/301
[58] Field of Search ................................... 356/301, 326, 356/328, 330–334, 419

[56] References Cited

U.S. PATENT DOCUMENTS

| | | |
|---|---|---|
| 3,042,542 | 7/1962 | Anders . |
| 3,414,354 | 12/1968 | Siegler, Jr. . |
| 3,556,659 | 1/1971 | Hawes . |
| 3,571,607 | 3/1971 | Giordmaine et al. . |
| 3,704,951 | 12/1972 | Chupp . |
| 3,704,955 | 12/1972 | Siegler, Jr. . |
| 3,723,007 | 3/1973 | Leonard . |
| 3,770,350 | 11/1973 | Stone et al. . |
| 3,797,942 | 3/1974 | Joly ............................... 356/419 |
| 3,807,862 | 4/1974 | Hatzenbuhler . |
| 3,877,818 | 4/1975 | Button et al. . |
| 4,068,953 | 1/1978 | Harney et al. . |
| 4,176,916 | 12/1979 | Carpenter . |
| 4,410,271 | 10/1983 | Matthews ......................... 356/301 |
| 4,573,761 | 3/1986 | McLachlan et al. . |
| 4,615,619 | 10/1986 | Fateley ............................ 356/310 |
| 4,630,923 | 12/1986 | Tans et al. ........................ 356/301 |
| 4,648,714 | 3/1987 | Benner et al. ..................... 356/301 |
| 4,676,639 | 6/1987 | Van Wagenen ..................... 356/246 |
| 4,697,924 | 10/1987 | Akiyama .......................... 356/333 |
| 4,750,834 | 6/1988 | Fateley ............................ 356/346 |
| 4,781,458 | 11/1988 | Angel et al. ...................... 356/301 |
| 4,784,486 | 11/1988 | Van Wagenen et al. ............. 356/301 |
| 4,799,795 | 1/1989 | Fateley ............................ 356/310 |
| 4,802,761 | 2/1989 | Bowen et al. ..................... 356/301 |
| 4,856,897 | 8/1989 | Fateley et al. ..................... 356/301 |
| 4,953,976 | 9/1990 | Adler-Golden et al. ............. 356/301 |
| 5,011,284 | 4/1991 | Tedesco et al. .................... 356/301 |
| 5,042,893 | 8/1991 | Ong ................................ 356/328 |
| 5,048,959 | 9/1991 | Morris et al. ..................... 356/301 |
| 5,112,127 | 5/1992 | Carrabba et al. ................... 356/301 |
| 5,135,304 | 8/1992 | Miles et al. ....................... 356/301 |
| 5,144,498 | 9/1992 | Vincent ............................ 359/885 |
| 5,153,670 | 10/1992 | Jannson et al. .................... 356/301 |
| 5,153,671 | 10/1992 | Miles .............................. 356/301 |
| 5,185,521 | 2/1993 | Kvasnik et al. .................... 356/301 |
| 5,194,913 | 3/1993 | Myrick et al. ..................... 356/301 |
| 5,221,957 | 6/1993 | Jannson et al. .................... 356/301 |
| 5,243,983 | 9/1993 | Tarr et al. ...................... 356/301 X |
| 5,245,405 | 9/1993 | Mitchell et al. ................... 356/301 |
| 5,381,237 | 1/1995 | Sela ............................... 356/301 |

FOREIGN PATENT DOCUMENTS

| | | |
|---|---|---|
| 2000305 | 4/1990 | Canada . |
| 0557658 | 9/1993 | European Pat. Off. . |
| 0557655 | 9/1993 | European Pat. Off. . |
| 2937352 | 6/1981 | Germany . |
| 2723939 | 1/1983 | Germany . |
| 47-28956 | 7/1972 | Japan ............................. 356/301 |
| WO9007108 | 6/1990 | WIPO . |

OTHER PUBLICATIONS

Weber et al, "High Resolution Raman Spectroscopy of Gases with Laser Sources, V. Use of the Single–Mode Argon Laser" *Journal of the Optical Society of America*, vol. 62, No. 3 Mar. 1972.

Pemberton et al., "Raman Spectroscopy Using Charge–Coupled Device Detection", *Spectroscopy*, vol. 5., No. 2, 1990, 2 pages.

Wang et al., "Evaluation of a Diode Laser/Charge Coupled Device Spectrometer for Near–Infrared Raman Spectroscopy", *Anal. Chem.*, 61, 1989, p. 2647.

Pemberton et al., "Raman Spectroscopy with Helium–Neon Laser Excitation and Charge–Coupled Device Detection", *J. Am. Chem. Soc.*, 1988, 1 page.

Hickman et al., "Intracavity Laser Raman Spectroscopy Using a Commercial Laser", *Applied Spectroscopy*, vol. 27, No. 6, 1973, pp. 425–427.

Hercher et al., "An Efficient Intracavity Laser Raman Spectrometer", *Applied Spectroscopy*, vol. 32, No. 3, 1978, pp. 298–301.

Neely et al., "Modification of a Commercial Argon Ion Laser for Enhancement of Gas Phase Raman Scattering", *Applied Spectroscopy*, vol. 26, No. 5, 1972, pp. 553–555.

Demtröder, *Laser Spectroscopy, Basic Concepts and Instrumentation,* Springer–Verlag, New York 1981, pp. 652–654.

Weber et al., "High–Resolution Raman Spectroscopy of Gases with cw–Laser Excitation", *Journal of the Optical Society of America,* vol. 57, No. 1, Jan. 1967, pp. 19–28.

Barrett et al.,"Laser–Excited Rotation–Vibration Raman Scattering in Ultra–Small Gas Samples", *Journal of the Optical Society of America,* vol. 58, No. 3, Mar. 1968, pp. 311–319.

Van Wagenen et al., "Dedicated Monitoring of Anesthetic and Respiratory Gases by Raman Scattering", *Journal of Clinical Monitoring,* vol. 2, No. 4, Oct. 1986, pp. 215–222.

D. A. Long, *Raman Spectroscopy,* McGraw–Hill, New York, 1977, Ch. 6 "Experimental Procedures", pp. 132–145.

Weber, *Raman Spectroscopy of Gases and Liquids,* Springer–Verlag, New York 1979, Ch. 3 "High–Resolution Rotational Raman Spectra of Gases", pp. 71–85.

Weber, *The Raman Effect, vol. 2: Applications,* Marcel Dekker, New York, 1973, Ch. 9 "High Resolution Raman Studies of Gases", pp. 543, 581, 586–589, 604–609, 611, 612, 617–622.

Barrett, *Laser Raman Gas Diagnostics,* Plenum Press, New York, 1974 "The Use of a Fabry–Perot Interferometer for Studying Rotational Raman Spectra of Gases", pp. 63–73.

Schrötter et al. *Raman Spectroscopy of Gases and Liquids,* Springer–Verlag, New York, 1979, Ch. 4 "Raman Scattering Cross Sections in Gases and Liquids", pp. 123, 124, 130–142.

Hill et al., *Laser Raman Gas Diagnostics,* Plenum Press, New York, 1974, "Raman Scattering with High Gain Multiple–Pass Cells", pp. 315–329.

Schiel et al., "Use of Raman Spectroscopy in Gas Analysis", *Fresenius Z. Anal. Chem.,* 327, 1987, pp. 335–337.

Albrecht et al., "Entwicklung Eines Raman–Spektroskopischen Gasanalysesystems", *Biomed. Technik,* 22, 1977, pp. 361–362 (with English translation).

Hendra et al, "Fourier Transform Raman Spectroscopy", Chapter 3, pp. 49–50, 1991.

*Primary Examiner*—Vincent P. McGraw
*Assistant Examiner*—K. P. Hantis
*Attorney, Agent, or Firm*—Roger M. Rathbun; Dennis H. Epperson; Larry R. Cassett

[57] ABSTRACT

A method and apparatus for determining the composition and concentration of gases present in a gas sample by measurement of the spectrum of Raman scattered light from these gases. A diode laser illuminates the unknown gas which is contained inside a long hollow tube having a highly reflective interior wall. A laser line pass filter at an entrance aperture of the hollow tube prevents all wavelengths except specific wavelengths characteristic of the laser from entering the long hollow tube. The laser beam and Raman scattered light from the gas sample reflect inside the hollow tube from the highly reflective interior wall. A laser line rejection filter at an exit aperture of the hollow tube prevents the laser beam from exiting the hollow tube but transmits the Raman scattered light from the gas sample. A spectrograph detector or array of discrete filters and detectors detects the Raman scattered light. The output of the detector(s) is then analyzed to identify the constituents of the unknown gas sample and the concentrations of the constituents.

47 Claims, 8 Drawing Sheets

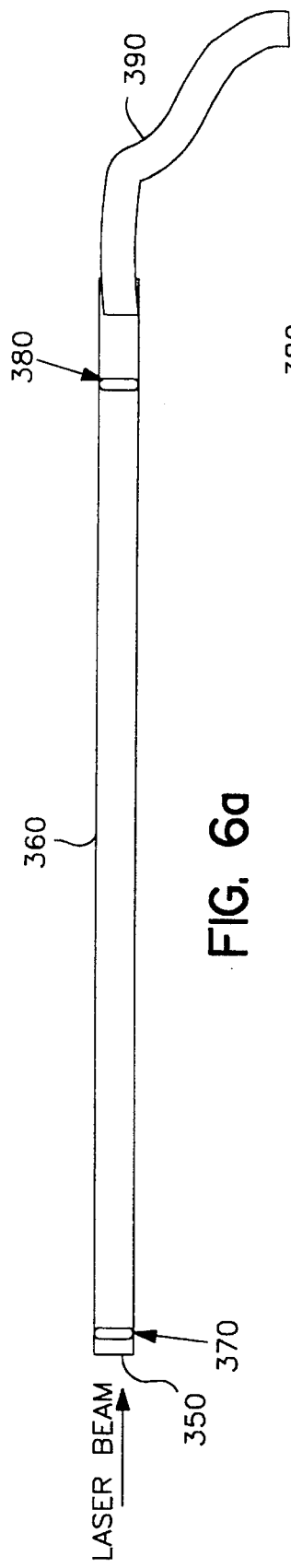
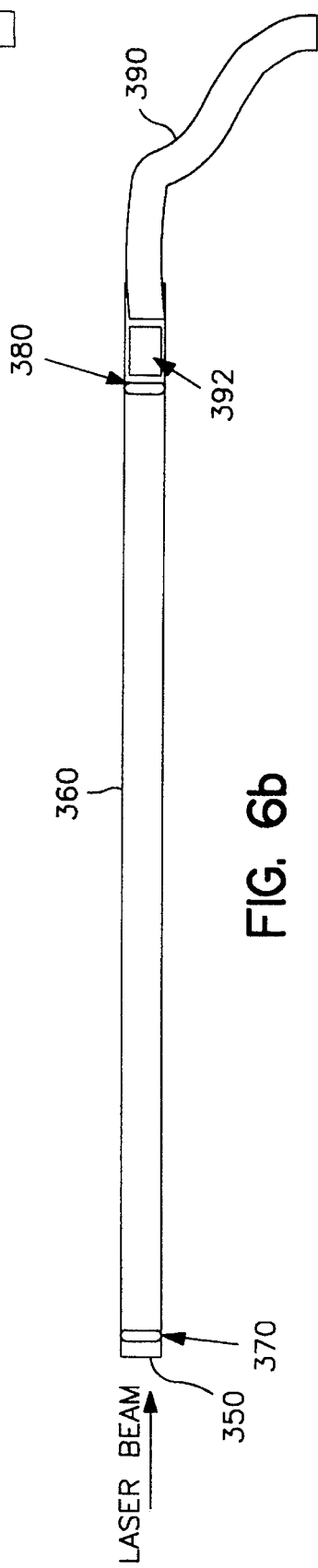
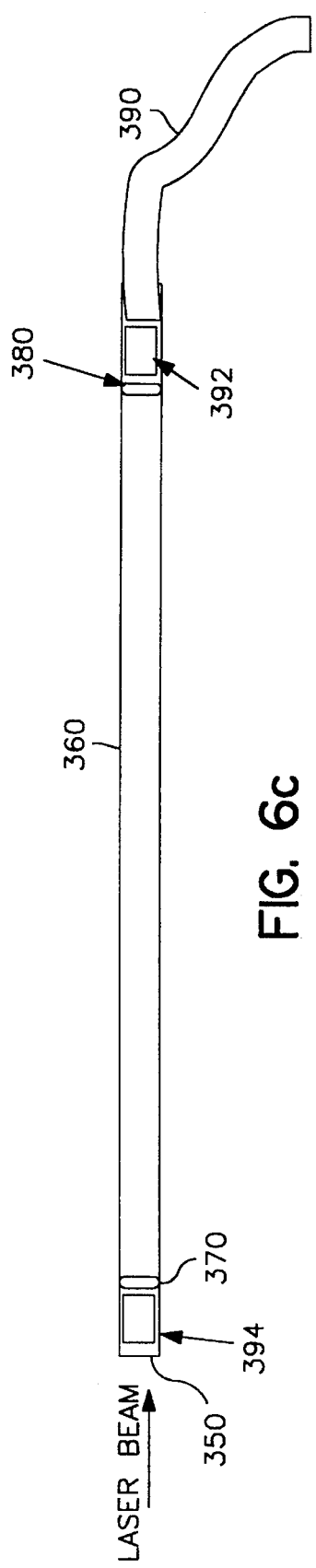

DIODE LASER PUMPED RAMAN GAS ANALYSIS SYSTEM WITH REFLECTIVE HOLLOW TUBE GAS CELL

FIELD OF THE INVENTION

The invention relates generally to gas analysis using Raman scattering and more specifically, to a gas analysis system having a laser diode pumped reflective hollow tube gas analysis cell. The present invention may be used in conjunction with conventional discrete or spectrometric detectors to perform molecular gas analysis in a variety of applications.

BACKGROUND OF THE INVENTION

Raman light scattering has been successfully used in critical care situations to continuously monitor a patient's respiratory gases. This technique is based on the effect which occurs when monochromatic light interacts with vibrational/rotational modes of gas molecules to produce scattered light which is frequency shifted from that of the incident radiation by an amount corresponding to the vibrational/rotational energies of the scattering gas molecules. If the incident light photon loses energy in the collision, it is re-emitted as scattered light with lower energy and consequently lower frequency than the incident photon. In a similar manner, if the incident photon gains energy in the collision, it is re-emitted as scattered light with higher energy and higher frequency than the incident photon. Since these energy shifts are species-specific, analysis of the various frequency components present in the Raman scattering spectrum of a sample provides chemical identification of the gases present in the scattering volume. The intensity of the various frequency components or Raman spectral lines provides quantification of the gases present, providing suitable calibrations have been made. In this manner, Raman light scattering can be employed to determine the identity and quantity of various respiratory and anesthetic gases present in a patient's breath in operating room and intensive care situations.

In addition to critical care situations, Raman light scattering gas analysis can also be used in many industrial applications such as stack gas analysis for combustion control, process control, fermentation monitoring, and pipeline gas mixture control. This analysis technique can also be extended to meet environmental monitoring needs in many areas such as escaped anesthetic agents in the operating room, air pollution, auto emissions testing and submarine atmosphere monitoring.

Systems developed for analysis of gases in critical care situations utilizing Raman scattering typically employ gas cells which contain a sample of the patient's respiratory gas to be analyzed. The gas sampling cell is located either within the resonant cavity of a laser or outside the cavity. In an intracavity system, a laser beam is directed through the resonant cavity such that it intercepts the gas within the sampling cell. Raman scattered light from the gas analysis region within the cell is collected and analyzed by conventional discrete or spectrometric detectors to perform molecular gas analysis.

At the center of these systems is the Raman scattering phenomenon which produces scattered radiation of a very weak intensity. There has been a long felt need to improve the efficiency, i.e., the signal to noise ratio, and lower the cost of Raman scattering based instruments, but progress has been hindered by the weak intensity of the scattered radiation and the numerous sources of noise.

One source of extraneous background is the laser. This background is detrimental in that it adds noise to the signal. In a gas laser, the laser produces not only the desired laser light at a specific wavelength, but also a broad spectrum of light sometimes called plasma glow. Similarly, a diode laser emits light over a wide region of the wavelength spectrum, sometimes called spontaneous emission, in addition to the wavelength specific laser line(s). Some of the extraneous light from either type of laser, plasma glow or spontaneous emission, often overlaps the wavelengths of Raman scattered light of interest and can even overwhelm the Raman scattering.

Another source of system background is often due to the optical elements in the system. For example, if lenses or other optical elements are used to collect and shape light emitted by the laser, the interaction of the laser light with the lenses and elements may produce output fluorescence and Raman scattering characteristic of the materials in the lenses and elements. This output fluorescence and Raman scattering from the lenses and other optical elements can overwhelm out the Raman signals produced by the gas sample being analyzed. Optical filters, often used in Raman scattering systems, are also potential sources of extraneous fluorescence and Raman scattering. Typically, a filter comprises a filter coating which is deposited on a supporting substrate, for example glass. In order to prevent the filter coating from absorbing moisture from the air, it may be sandwiched between two glass plates and sealed around the edges. However, if such a filter is used in a Raman gas analysis system where the laser light interacts with the filter, the fluorescence and Raman scattering generated as the laser passes through the glass can produce extraneous light which can overwhelm the Raman scattering from the gas sample. This occurs even if a low fluorescing glass such as fused silica is used.

The device disclosed in European Patent Application publication number 0 557 655 A1 entitled "SYSTEM FOR COLLECTING WEAKLY SCATTERED OPTICAL SIGNALS" describes a system for enhancing the collection efficiency of a gas analysis system. This document discloses a system having a laser which illuminates an unknown gas contained by a long hollow chamber having a highly reflective coating. A laser beam propagates along the longitudinal dimension of the interior region of the long hollow chamber without contacting the reflective coating. The reflective coating, either on the inner or outer surface of a transparent hollow tube, is designed to reflect radiation which is scattered from the laser beam by the unknown gas contained within the long hollow chamber, thus enhancing the collection efficiency for light produced by the interaction of the laser beam with the gas sample, e.g. Raman scattered light. The laser beam is specifically prevented from interacting with the reflective coating since such interactions produce not only a reflected laser beam, but a weak collateral radiation, e.g. fluorescence and Raman scattering as discussed previously. This weak collateral radiation is unwanted because it tends to interfere with the measurement of the radiation scattered by the unknown gas. Thus, the approach taken by this reference for reducing the effect of the weak collateral radiation produced by the laser and by the interaction of the laser with reflective coatings and filters is to minimize such interactions by directing the laser beam along the longitudinal axis such that the laser beam does not interact with the reflective coating. Additionally, interactions with filters are eliminated by not having any filters in the laser beam path. While this approach may succeed in reducing collateral radiation due to interactions of the laser beam with the walls and/or reflective coating of the long hollow chamber, it also limits the kind of lasers which can be used. This is due to the tight collimation required to keep the incident laser light away from the walls and/or reflective coating of the long hollow chamber. It is difficult to produce a narrow, collimated beam with high powered diode lasers, thus reducing the intensity of light on the gas sample.

U.S. Pat. No. 3,556,659 entitled "LASER-EXCITED RAMAN SPECTROMETER" discloses a laser-excited Raman spectrometer in which a laser output beam having a very small diameter is projected along the length of a capillary sample cell, rather than being projected in a transverse direction. The beam is substantially coaxial with the cell and the resultant Raman scattered light travelling in the general direction of the cell axis is detected. This reference also emphasizes the importance of confining the laser beam to the capillary bore, with very little of it traversing the capillary wall. This is done to minimize the scattering of the laser radiation from the cell wall and excitation of fluorescence in the cell wall. It is also noted that aligning the laser beam with the capillary bore requires accurate alignment but is worth the effort because it minimizes fluorescence of the glass wall and scattering of light from the wall itself.

The device disclosed in European Patent Application publication number 0 557 658 A1 entitled "RAMAN SPECTROSCOPY OF RESPIRATORY GASES" describes a system for determining the composition and concentration of gases present in a patient's airway by measurement of the spectrum of Raman scattered light from these gases. The gases present are assumed to be drawn from a predetermined set of gases with known Raman scattering spectra, and the concentrations are determined by solution of a matrix equation $Ac=b$, where the c vector components are the unknown concentrations and the b vector components are determined from measurements of the Raman scattering intensities in a plurality of wavelength or wavenumber intervals. The gas sample flows through an optical waveguide similar to that disclosed in previously discussed European Patent Application publication number 0 557 655 A1. Collection optics including mirrors and filters direct the Raman scattered light from the sample into a diffraction grating spectrometer. The composition of the gas mixture is determined by analyzing the measured spectrum, which represents the sum of the spectra of the individual gases, weighted by the concentration of each gaseous component. Since this system utilizes components which are the same or similar to those disclosed in European Patent Application publication number 0 557 655 A1, i.e., the optical waveguide wherein the gas sample interacts with the laser, it also exhibits similar shortcomings. Additionally, as with any optical system, the collection and transportation of light from the optical waveguide to the spectrometer with mirrors and/or lenses is inherently inefficient.

What is needed is a gas monitoring system that: 1) reduces the level of non-laser light which is detected along with the desired Raman scattered light from the gas sample; 2) reduces extraneous fluorescence and Raman scattering produced by the interaction of the laser light with system components; and 3) efficiently couples the desired Raman scattered light from the gas sample to a detector or spectrometer.

SUMMARY OF THE INVENTION

The present invention is a gas monitoring system having a hollow reflective tube that: 1) reduces the level of non-laser light which is detected along with the desired Raman scattered light from the gas sample; 2) reduces extraneous fluorescence and Raman scattering produced by the interaction of the laser light with system components; and 3) efficiently couples the desired Raman scattered light from the gas sample to a detector or spectrometer.

In a first embodiment, the present invention is an apparatus for the analysis of gases in a gas sample by Raman light scattering comprising: a laser light source for producing and transmitting a laser beam of optical radiation along a longitudinal axis; a gas sample cell to receive and hold the gas sample along the longitudinal axis in an interior region of the gas cell, wherein the gas sample cell is positioned to receive the laser beam of optical radiation from the laser light source via a first end of the gas sample cell, the gas sample cell further having a second end and a highly reflective interior surface suitable for reflecting the laser beam and Raman scattered light from the gas sample; a laser line pass filter which transmits a narrow wavelength band of light centered on a laser line characteristic of the laser light source, wherein the laser line pass filter is positioned at the first end of the gas sample cell thereby transmitting that portion of the laser beam containing the characteristic laser line into the gas sample cell and rejecting substantially all other wavelengths comprising the laser beam; a laser line rejection filter which transmits substantially all wavelengths except the narrow wavelength band of light centered on the laser line characteristic of the laser light source, wherein the laser line rejection filter is positioned at the second end of the gas sample cell thereby transmitting light scattered by the gas sample at wavelengths different from the wavelength of the laser line characteristic of the laser light source out of the gas sample cell and reflecting the laser beam back through the sample cell; and a detector optically connected to the second end of the gas cell for receiving and detecting the light scattered from the gas sample and transmitted through the laser line rejection filter. The laser light source may further comprise a diode laser. In some embodiments, the gas sample cell may be an elongate hollow tube having a substantially uniform interior diameter and a length which is substantially greater than the interior diameter. Additionally, the highly reflective interior surface of the gas sample cell may comprise a metallic material. More specifically, the highly reflective interior surface of the gas sample cell may be gold. Additionally, the laser line pass filter may comprise a filter coating formed on a substrate. The laser line pass filter is positioned immediately adjacent to the first end of the gas sample cell thereby closing the first end of the gas sample cell. Furthermore, the laser line pass filter is positioned adjacent the first end of the gas sample cell such that the filter coating faces the interior region of the gas sample cell. Additionally, a preferred embodiment comprises a filter coating which is substantially non-hydrophilic. One such non-hydrophilic filter coating comprises tantalum. Another such non-hydrophilic filter coating comprises silicon dioxide. In yet another embodiment, the laser line rejection filter comprises a filter coating formed on a substrate. The laser line rejection filter is positioned immediately adjacent to the second end of the gas sample cell thereby closing the second end of the gas sample cell. Furthermore, the laser line rejection filter is positioned adjacent the second end of the gas sample cell such that the filter coating faces the interior region of the gas sample cell. In some embodiments, the detector comprises a spectrograph. Some embodiments further comprise a lens system positioned intermediate the laser light source and the gas sample cell, the lens collecting and focusing the laser beam of optical radiation from the laser light source and directing the laser beam of optical radiation into the first end of the gas sample cell. This lens may further comprise a gradient index of refraction (GRIN) lens. Additionally, some embodiments further comprise an optical fiber positioned intermediate the gas sample cell and the detector, the optical fiber transmitting the light scattered by the gas sample at wavelengths different from the wavelength of the laser line characteristic of the laser light source out of the gas sample cell into the detector. Some embodiments further comprise a light guide positioned intermediate the gas sample cell and the detector, the optical fiber transmitting the light scattered by the gas sample at wavelengths different from the wavelength of the laser line characteristic of the laser light source out of the gas sample cell into the detector. In some embodiments, the gas sample cell further comprises a gas input port and a gas output port. In yet another embodiment, the invention further comprises an optical fiber positioned intermediate the gas sample cell and the detector, the optical fiber having an input and a plurality of outputs, wherein each output transmits a portion of the light scattered by the gas sample at wavelengths different from the wavelength of the laser line characteristic of the laser light source out of the gas sample cell into a detector channel.

In a second embodiment, the present invention is an apparatus for the analysis of gases in a gas sample by Raman light scattering comprising: a hollow tube for holding a sample of a gas to be analyzed, the hollow tube having a highly reflective interior tubular wall enclosing a bore forming a sample region, the bore having a length that is at least five times greater than its diameter, the bore having a longitudinal axis along its length; a laser light source for producing and transmitting a laser beam of optical radiation into the hollow tube bore through a first end of the hollow tube such that a first portion of the beam of optical radiation propagates through the bore along the bore longitudinal axis and a second portion of the beam of optical radiation propagates through the bore by reflecting from the highly reflective interior tubular wall; a laser line pass filter which transmits a narrow wavelength band of light centered on a laser line characteristic of the laser light source, wherein the laser line pass filter is positioned at the first end of the hollow tube thereby transmitting that portion of the laser beam containing the characteristic laser line into the bore and rejecting substantially all other wavelengths comprising the laser beam; a laser line rejection filter which transmits substantially all wavelengths except the narrow wavelength band of light centered on the laser line characteristic of the laser light source, wherein the laser line rejection filter is positioned at a second end of the hollow tube thereby transmitting light scattered by the gas sample at wavelengths different from the wavelength of the laser line characteristic of the laser light source out of the hollow tube bore and reflecting the laser beam back through the hollow tube bore; and a detector optically connected to the second end of the hollow tube for receiving and detecting the light scattered from the gas sample and transmitted through the laser line rejection filter. In another aspect of this embodiment the laser light source comprises a diode laser. Additionally, the highly reflective interior tubular wall of the hollow tube may comprise a metallic material, for example gold. In another aspect of the second embodiment, the laser line pass filter comprises a filter coating formed on a substrate, wherein the laser line pass filter is positioned immediately adjacent to the first end of the hollow tube thereby closing the first end of the hollow tube. The laser line pass filter is positioned adjacent the first end of the hollow tube such that the filter coating faces the sample region of the hollow tube. In other aspects of the second embodiment the filter coating is substantially non-hydrophilic and may comprise, for example tantalum and/or silicon dioxide. In yet another aspect of the second embodiment, the laser line rejection filter comprises a filter coating formed on a substrate, the laser line rejection filter positioned immediately adjacent to the second end of the hollow tube thereby closing the second end of the hollow tube, the laser line rejection filter positioned adjacent the second end of the hollow tube such that the filter coating faces the sample region of the hollow tube. In another aspect of the second embodiment, the detector comprises a spectrograph. Yet another aspect of the second embodiment further comprises a lens positioned intermediate the laser light source and the hollow tube, the lens collecting and focusing the laser beam of optical radiation from the laser light source and directing the laser beam of optical radiation into the first end of the hollow tube. This lens may further comprise a gradient index of refraction (GRIN) lens. Other versions of the second embodiment include an optical fiber positioned intermediate the hollow tube and the detector, the optical fiber transmitting the light scattered by the gas sample at wavelengths different from the wavelength of the laser line characteristic of the laser light source out of the hollow tube into the detector. Another aspect of the present invention, further comprises a light guide positioned intermediate the hollow tube and the detector, the optical fiber transmitting the light scattered by the gas sample at wavelengths different from the wavelength of the laser line characteristic of the laser light source out of the hollow tube into the detector. In another aspect of the second embodiment, the hollow tube further comprises a gas input port and a gas output port. Yet another aspect of the second embodiment further comprises an optical fiber positioned intermediate the hollow tube and the detector, the optical fiber having an input and a plurality of outputs, wherein each output transmits a portion of the light scattered by the gas sample at wavelengths different from the wavelength of the laser line characteristic of the laser light source out of the hollow tube into a separate detector channel.

The present invention further includes a method of analyzing a gas sample comprising the steps of: providing a laser which produces a laser beam which propagates substantially along a longitudinal axis; providing a laser line pass filter in the path of the laser beam which transmits a specific wavelength characteristic of the laser; directing the filtered laser beam through a first end of a hollow tube having a longitudinal axis which is substantially aligned with the laser beam longitudinal axis wherein the hollow tube confines the gas sample inside a region surrounded by a highly reflective surface so that the filtered laser beam propagates through the sample such that a portion of the filtered laser beam reflects from the highly reflective surface of the hollow tube while propagating through the sample; providing a laser line rejection filter at a second end of the hollow tube which transmits a wavelength band including Raman lines characteristic of the constituents of the gas sample and reflects the specific wavelength characteristic of the laser; and detecting and analyzing the Raman lines which are characteristic of the constituents of the gas sample to identify the constituents.

Yet another embodiment of the invention is an apparatus for the analysis of gases in a gas sample by Raman light scattering comprising: a laser light source for producing and transmitting a laser beam of optical radiation along a longitudinal axis; a gas sample cell to receive and hold the gas sample along the longitudinal axis in an interior region of the gas cell, wherein the gas sample cell is positioned to receive the laser beam of optical radiation from the laser light source via a first end of the gas sample cell, the gas sample cell further having a second end and a highly reflective interior surface suitable for reflecting the laser beam and Raman scattered light from the gas sample; a laser line pass filter which transmits a narrow wavelength band of light centered on a laser line characteristic of the laser light source, wherein the laser line pass filter is positioned at the first end of the gas sample cell thereby transmitting that portion of the laser beam containing the characteristic laser line into the gas sample cell and rejecting substantially all other wavelengths comprising the laser beam; a subtractive dispersion laser line rejection filter which transmits a band of wavelengths including the Raman line of interest but excluding the wavelength characteristic of the laser light source, wherein the subtractive dispersion laser line rejection filter is positioned at the second end of the gas sample cell thereby transmitting light scattered by the gas sample at wavelengths different from the wavelength of the laser line characteristic of the laser light source out of the gas sample cell; and a detector optically connected to the second end of the gas cell for receiving and detecting the light scattered from the gas sample and transmitted through the laser line rejection filter. In this embodiment, the subtractive dispersion laser line rejection filter may further comprise: a first diffraction grating which receives light from the second end of the sample cell; a first intermediate slit which receives light from the first diffraction grating and transmits the Raman scattered light and blocks the laser line; a second diffraction grating which receives light from the first intermediate slit and recombines the dispersed wavelengths; and a second intermediate slit which receives light from the second diffraction grating and transmits the Raman scattered light. In some embodiments, the second diffraction grating is the reciprocal of the first diffraction grating. In some embodiments, the second intermediate slit is narrower than the first intermediate slit.

These and other characteristics of the present invention will become apparent through reference to the following detailed description of the preferred embodiments and accompanying drawings.

BRIEF DESCRIPTION OF THE DRAWINGS

FIGS. 6a, 6b and 6c are schematic diagrams illustrating second, third and fourth alternative embodiments of the present invention.

DETAILED DESCRIPTION OF THE PREFERRED EMBODIMENTS

Figure 1:
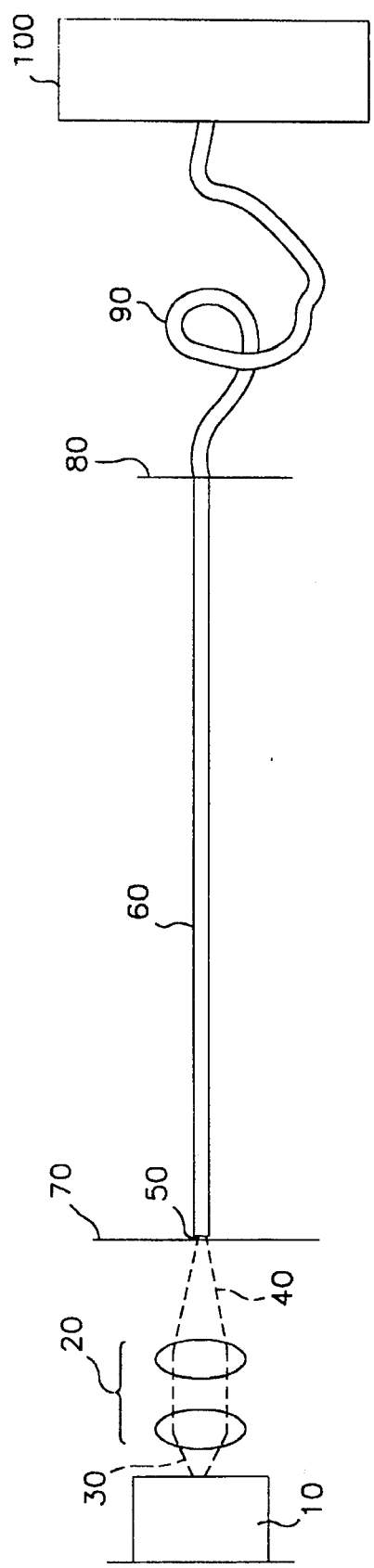
FIG. 1 is a schematic diagram illustrating a preferred embodiment of the present invention having a fiber optic coupling to a conventional spectrograph.

In the embodiment of the invention illustrated in FIG. 1, light is produced by a diode laser 10. Beam shaping optics 20 collect the diode laser output 30, shape it appropriately, and direct the light 40 towards an aperture 50 in a proximate end of a hollow reflective tube 60. Before entering the hollow reflective tube 60 the light 40 passes through a dielectric filter 70 that allows only a narrow wavelength band centered on the laser line to pass through the filter 70 and enter the hollow reflective tube 60 through the aperture 50. Thus, the filtered output from the diode laser 10 passes through the optical aperture 50 at the proximate end of the hollow reflective tube 60 into the hollow reflective tube 60. In some embodiments, the aperture 50 and filter 70 are combined such that the filter 70 allows the laser light to enter the hollow reflective tube 60 and also serves to seal the aperture 50 of the hollow reflective tube 60 thus confining a sample gas within the hollow tube 60. The laser light then propagates through the hollow reflective tube 60 occasionally reflecting off the interior walls of the reflective hollow tube 60. As the laser light propagates through the gas sample contained within the reflective hollow tube 60, some of the laser light is Raman scattered from the sample gas thereby generating Raman scattered light which has wavelengths that are characteristic of the constituents of the sample gas. A laser line rejection filter 80 is positioned at a distal end of the reflective hollow tube 60. Laser line rejection filter 80 is similar in construction to the band pass filter 70, but it passes the wavelengths of Raman scattered light comprising the Raman spectrum and rejects the laser wavelength. Thus, the Raman scattered light passes through the filter 80 while the laser light is reflected back through the reflective hollow tube 60. This reflected laser light again generates Raman scattering as it travels through the sample in a direction back towards the laser 10, effectively doubling the single pass power of the system. In the embodiment illustrated in FIG. 1, the light exiting the reflective hollow tube 60 is collected by a fiber bundle 90. A proximate end of fiber bundle 90 is the same size as the reflective hollow tube exit aperture and can be polished so the filter coating 80 can be deposited directly onto the proximate end of the fiber bundle 90. Thus, the proximate end of fiber bundle 90 serves three functions: 1) it couples the light exiting from the hollow reflective tube 60 into the fiber 90; 2) it seals the distal end of the reflective hollow tube 60 thus confining the gas sample therein; and 3) it provides a substrate to support the filter 80. The fiber bundle 90 has a distal end which is connected to a spectrograph 100. Preferably, the numerical aperture (N.A.) of the fiber bundle 90 is chosen to match the input numerical aperture of the spectrograph 100. For example, if the numerical aperture of the spectrograph 100 is 0.29, then the fiber bundle 90 is selected to have a numerical aperture of 0.29.

Figure 2A:
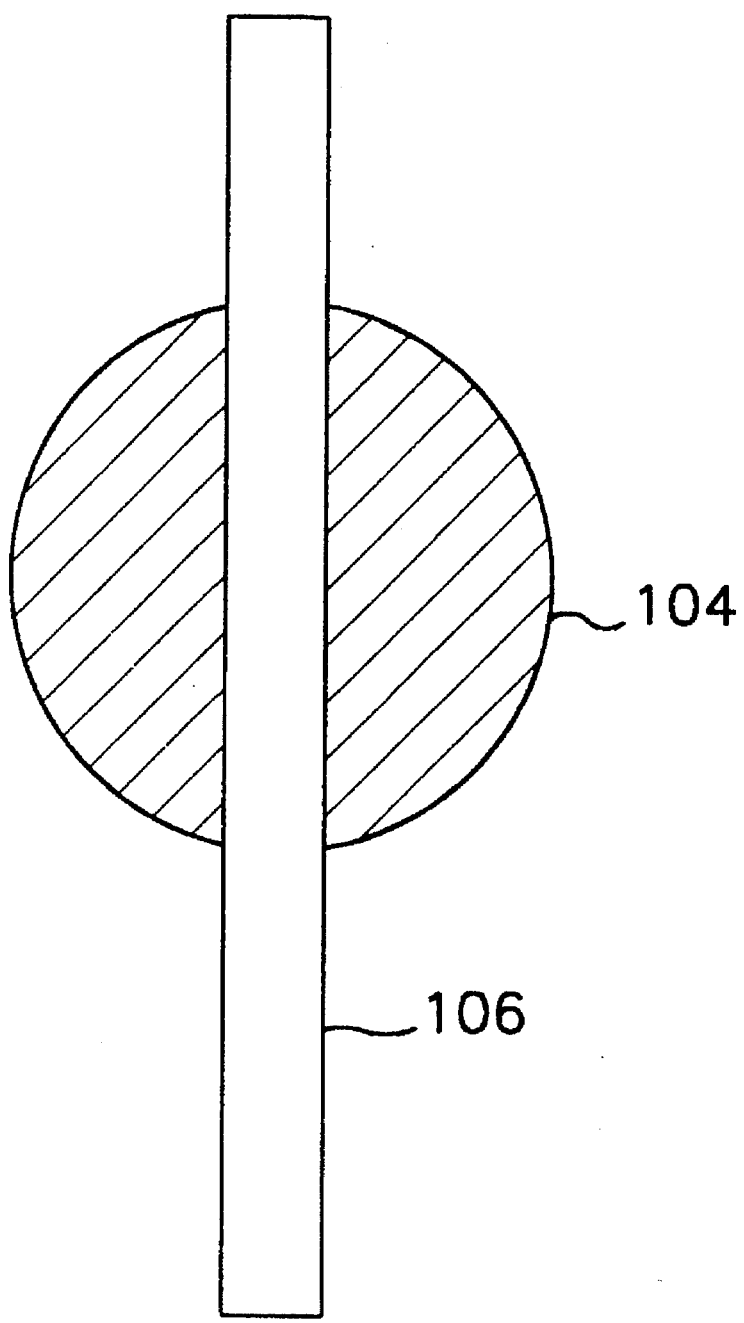
FIGS. 2a and 2b are schematic diagrams illustrating the efficiency of the fiber optic coupling of the present invention.
Figure 2B:
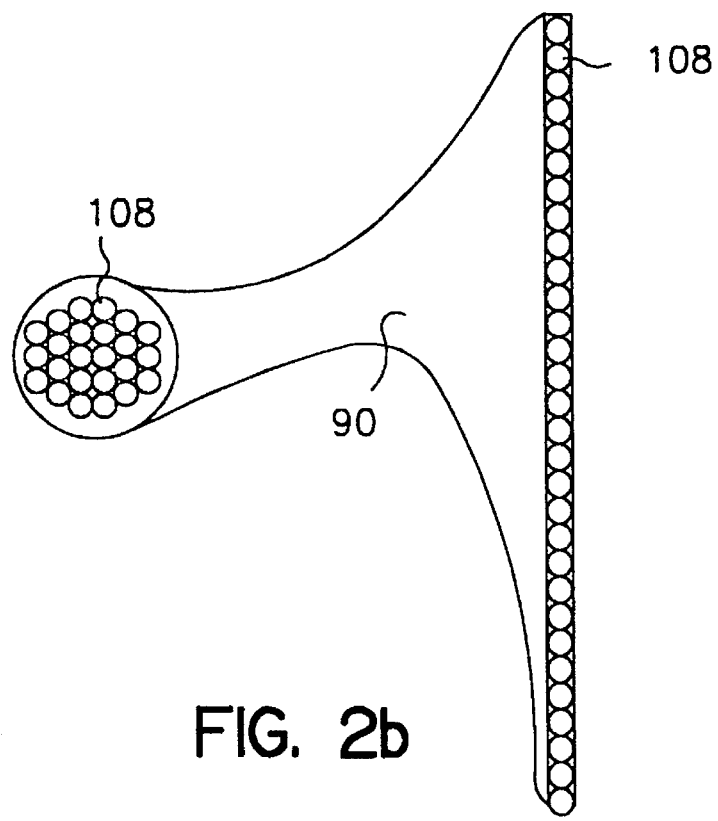

Collecting the light from the reflective hollow tube 60 and transporting it to the spectrograph 100 with the fiber bundle 90 is advantageous since the proximate end of the fiber bundle 90 can be circular to match the distal aperture of the hollow tube 60 and the distal end of the fiber bundle 90 can be a rectangular linear array to match the shape of the input slit of the spectrograph 100. In many applications, the linear array can serve as the entrance aperture, or the slit, of the spectrograph. Thus, the fiber bundle 90 may provide a simple and efficient means for transforming from the circular geometry of the hollow tube 60 to the narrow slit needed for the spectrograph. In one embodiment of the present invention, the fiber bundle 90 comprises 200 micron cores with a 20 micron cladding. The coupling efficiency of this configuration is illustrated in FIGS. 2a and 2b. As shown in FIG. 2a, if a circular tube end 104 is imaged directly onto a slit 106, only 25% (for a 1 mm tube and 200 micron slit) of the aperture 104 is imaged onto the slit 106. The use of a fiber bundle 90 is illustrated in FIG. 2b. Fiber cores 108 comprising the fiber bundle 90 occupy only a fraction of the usable area and scattered light that strikes other areas is not collected. The fraction of the area covered by the cores is typically approximately 65%, so almost 3 times more signal is collected with the circular-to-rectangular fiber bundle 90 than with direct imaging of a circular aperture onto a rectangular slit.

Figure 2C:
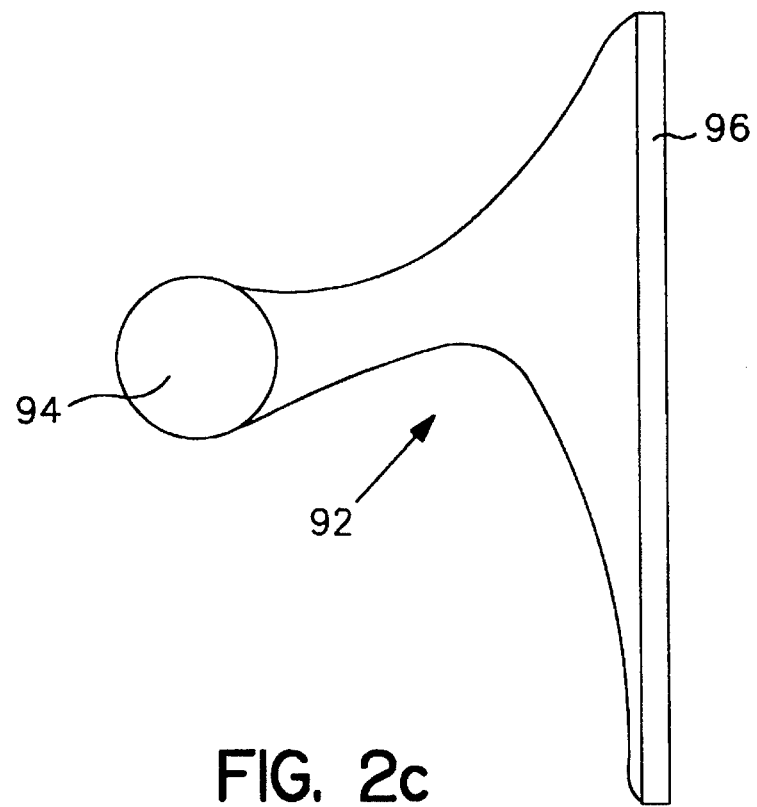
FIG. 2c is a schematic diagram illustrating a one piece circular-to-rectangular waveguide.

In another embodiment, shown in FIG. 2c, a one piece circular-to-rectangular waveguide 92 is used in place of the fiber bundle 90. Similar to the fiber bundle 90, the one piece circular-to-rectangular waveguide 92 has a round aperture 94 on one end and a rectangular aperture 96 on the other end. The dimensions of the round aperture 94 are matched to the distal aperture of the hollow reflective tube 60 and the dimensions of the rectangular aperture 96 match the dimensions of the input slit of the spectrograph 100. One advantage of the one piece waveguide 92 is that all of the area is used for collection and transmission of light as opposed to the fiber bundle 90 where only 65% of the area is used. A disadvantage is that the numerical aperture for light exiting the rectangular aperture 96 may be affected by changing from a circular shape to the elongated rectangle (6 mm×0.2 mm). Additionally, the one piece waveguide 92 may be less flexible than the fiber bundle 90.

There are several ways to produce the circular-to-rectangular waveguide 92. One way is to mold the circular-to-rectangular waveguide 92 out of glass or plastic into the exact shape desired. If a cladding layer is desired, the molded circular-to-rectangular waveguide 92 may be dipped in an appropriate material to produce the cladding layer. Another method of fabricating the circular-to-rectangular waveguide 92 is to take a glass or plastic circular waveguide, heat one end and press it into the desired rectangular shape.

Figure 3A:
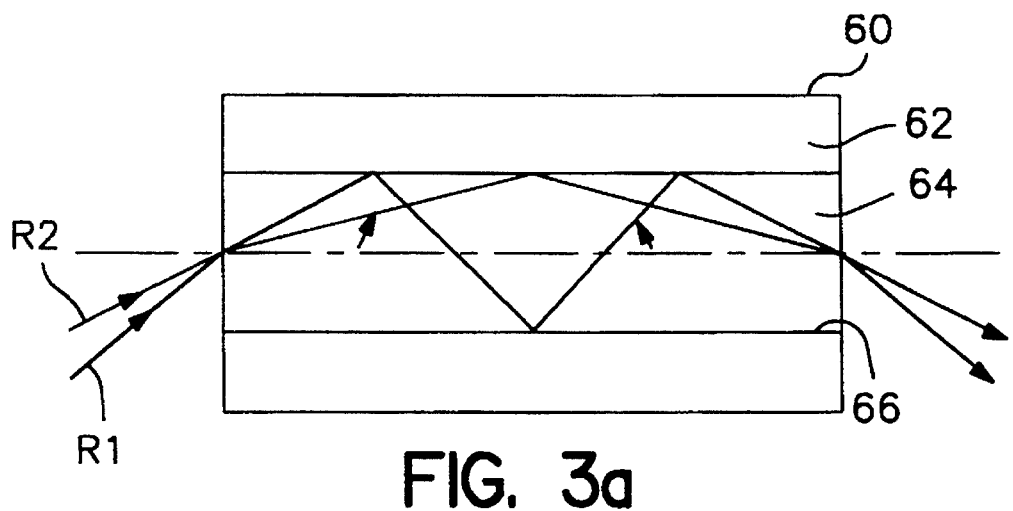
FIGS. 3a and 3b are schematic diagrams illustrating the paths of laser beam light rays through the reflective hollow tube of the present invention.
Figure 3B:
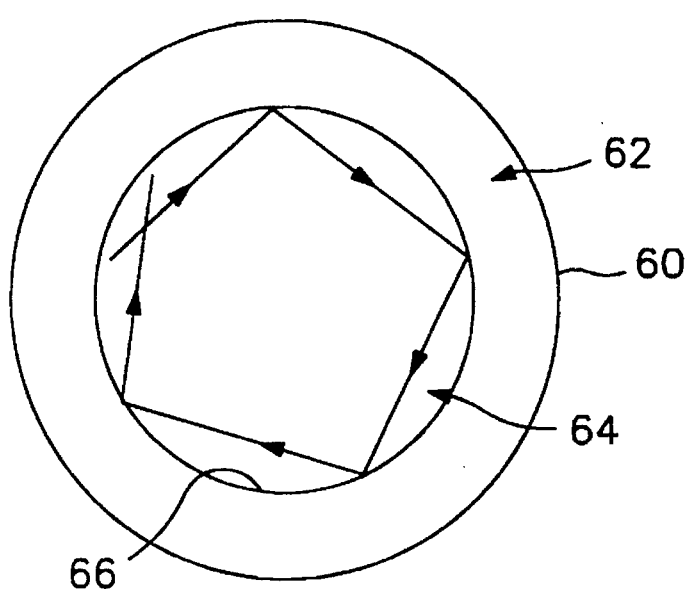

The importance of using a highly reflective hollow tube 60 to enhance the Raman scattered light signal is illustrated in FIGS. 3a and 3b and the data in Table 1. As shown in FIG. 3a, hollow tube 60 comprises a wall 62 surrounding a chamber 64. An interior surface 66 forms the boundary between the wall 62 and the chamber 64. The paths of two light rays, R1 and R2, propagating through the chamber 64 at different angles by reflecting off of the wall 62 are shown in FIG. 3a. If the light is focused into the tube 60 at f/#=f/2, the tube is 1 mm in diameter, and 6" long, the light is reflected at least 38 times for the steepest rays. In fact it will be many more reflections because the rays are spiraling down the tube as shown in FIG. 3b. Table 1 shows the fraction of power reaching the distal end of the tube for different reflection values of the wall 66 and different numbers of reflections. For example, for 37 reflections, the fraction of the input power reaching the distal end of the tube with a 90% reflective inner wall 66 is only 2% compared to 83% if the inner wall 66 is 99.9% reflective.

TABLE 1

Losses as a Function of the Number of Reflections and Reflectivity

| Number of Reflections | 90% Ref. | 95% Ref. | 98% Ref. | 99% Ref. | 99.9% Ref. |
| --- | --- | --- | --- | --- | --- |
| 1 | 90% | 95% | 98% | 99% | 100% |
| 3 | 73% | 86% | 94% | 97% | 99% |
| 5 | 59% | 77% | 90% | 95% | 98% |
| 7 | 48% | 70% | 87% | 93% | 97% |
| 9 | 39% | 63% | 83% | 91% | 96% |
| 11 | 31% | 57% | 80% | 90% | 95% |
| 13 | 25% | 51% | 77% | 88% | 94% |
| 15 | 21% | 46% | 74% | 86% | 93% |
| 17 | 17% | 42% | 71% | 84% | 92% |
| 19 | 14% | 38% | 68% | 83% | 91% |
| 21 | 11% | 34% | 65% | 81% | 90% |
| 23 | 9% | 31% | 63% | 79% | 89% |
| 25 | 7% | 28% | 60% | 78% | 88% |
| 27 | 6% | 25% | 58% | 76% | 87% |
| 29 | 5% | 23% | 56% | 75% | 86% |
| 31 | 4% | 20% | 53% | 73% | 86% |
| 33 | 3% | 18% | 51% | 72% | 85% |
| 35 | 3% | 17% | 49% | 70% | 84% |
| 37 | 2% | 15% | 47% | 69% | 83% |
| 39 | 2% | 14% | 45% | 68% | 82% |
| 41 | 1% | 12% | 44% | 66% | 81% |
| 43 | 1% | 11% | 42% | 65% | 81% |
| 45 | 1% | 10% | 40% | 64% | 80% |
| 47 | 1% | 9% | 39% | 62% | 79% |
| 49 | 1% | 8% | 37% | 61% | 78% |
| 51 | 0% | 7% | 36% | 60% | 77% |

Another result of the laser light spiraling through the chamber 64 of the tube 60 is that the polarization becomes scrambled. The resulting Raman scattered light is emitted in all directions but only those rays that don't go through too many reflections will exit the tube and be collected.

The hollow reflective tube 60 with a highly reflective inner surface 66 may be produced in many configurations. For example, it may comprise a glass tube with gold deposited on the inner surface. Gold is an excellent material because of it's high reflectivity above 650 nm and because it does not fluoresce or produce any Raman scattering. Silver also meets these criteria, but silver oxidizes over time (tarnishes) and this reduces the reflectivity. Silver can be overcoated with a protective dielectric layer to prevent oxidation, but this layer may produce Raman scattering and/or fluorescence and may reduce the reflectivity of the silver. Dielectric reflective coatings are less appropriate than the gold or silver because Raman scattering produced from the coating may overwhelm the desired Raman signal from the sample gas. Effective broadband dielectric reflective coatings are also difficult to produce for the grazing angles that occur in the tube. Coatings for the P-polarized light at grazing incidence are particularly problematical. Thus, metallic coatings are better suited for this system.

One such reflective tube having a gold alloy structure that sheaths the inner surface of a hollow glass tube can be ordered from Hewlett Packard as "replacement light pipe" part number 05965-60155. This part is used in the Hewlett Packard 5965B Infrared Detector.

Another reflective tube suitable for the present invention is a gold alloy tube available commercially from Epner Technology, Inc. in Brooklyn, N.Y.

Some prior art systems use a reflective coating on the outer surface of a glass tube. This is not optimum for the present system since the light must pass through the glass before being reflected. Undesired Raman scattering and fluorescence will be generated in the glass as the laser light travels through the glass before and after being reflected.

In addition to the laser light characteristic of the diode laser, diode lasers also emit light over a wide region of the wavelength spectrum. Included in this broad band emission is light referred to as spontaneous emission. A portion of the spontaneous emission light may overlap the Raman wavelengths of interest and can overwhelm the desired Raman scattering. Furthermore, if lenses are used to collect and shape the diode laser output prior to entering the reflective hollow tube 60, fluorescence and Raman scattering may be generated in the lenses and this light can also overwhelm the desired Raman signal. Thus, it is advantageous to position band pass filter 70 between the laser 10 and the reflective hollow tube 60. Furthermore, it is advantageous to use a specially designed filter to reduce extraneous signals. Typically, the filter coating is sandwiched between two glass plates and sealed around the edges to prevent the coating material from absorbing moisture from the surrounding air which can destroy the filter. However, if such a filter is used in a Raman gas analysis system, fluorescence and Raman scattering generated as the laser passes through the glass after it goes through the coating material can overwhelm the desired Raman scattering from the gas sample. This is true even if a low fluorescing glass, such as fused silica, is used. Therefore, the filter 70 should be made in such a way that the coating material will not absorb water from the surrounding atmosphere and be configured in a way which does not require the laser light to pass through any material except the filter material just prior to entering the hollow reflective tube 60. There are several methods to build this type of filter. One way is to use different coating materials that produce harder coatings that do not absorb water. Materials such as tantalum and $SiO_2$ produce such coatings. Another method is to use a different coating process, such as ion beam sputtering, that produces coatings that do not absorb water. Other methods and materials will be obvious to one skilled in the art of coatings. Finally, the filter should be oriented so that the coated surface faces the entrance aperture of the hollow reflective tube 60, thereby preventing fluorescence and Raman scattering produced in the filter substrate from entering the hollow reflective tube 60.

Figure 4:
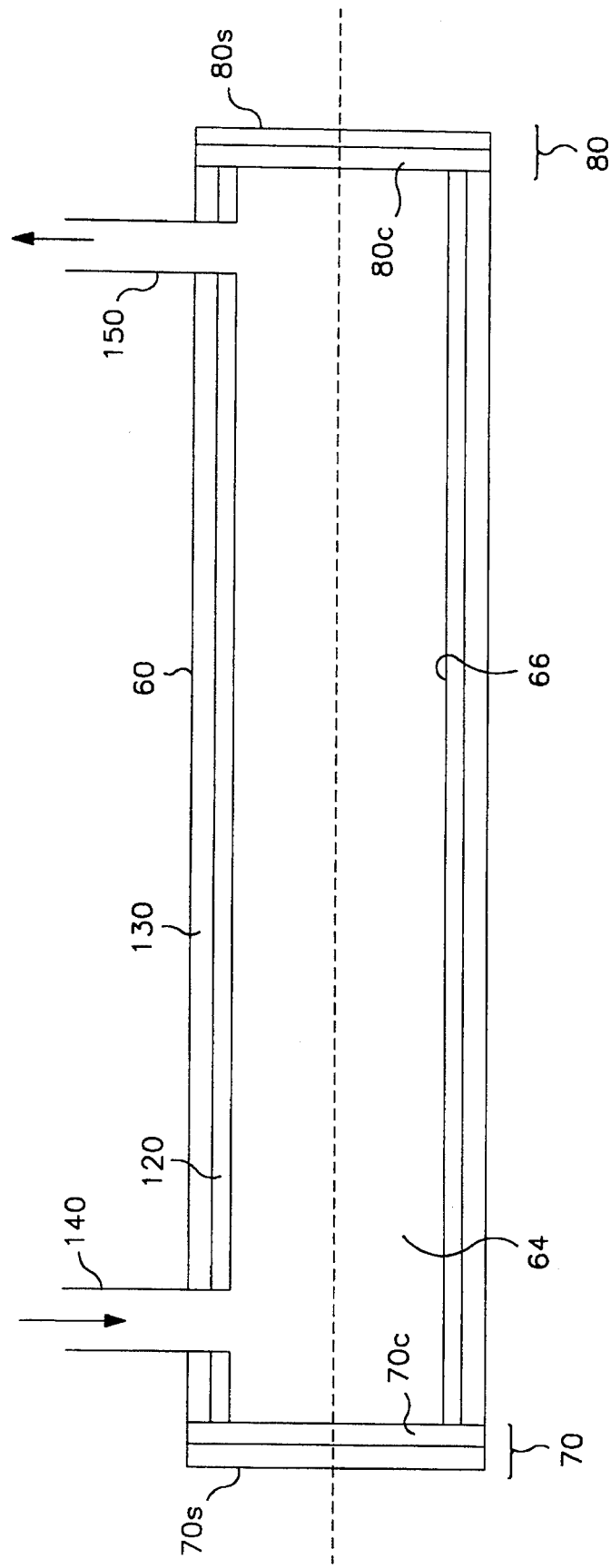
FIG. 4 is a cross section of the reflective hollow tube/gas cell of the present invention illustrating details thereof.

FIG. 4 illustrates a more detailed section view of the hollow reflective tube 60 of the present invention. The hollow reflective tube 60 includes a reflective inner layer 120 which forms the reflective inner surface 66 surrounded by a layer of sheath or substrate material 130. The chamber 64 in which the gas sample being analyzed is placed has an inlet port 140 and exit port 150 to allow the gas sample to be circulated through the chamber 64. Additionally, the laser line pass filter 70 and the Raman band pass/laser line rejection filter 80 are shown as having filter coating layers 70c and 80c and substrate layers 70s and 80s, respectively. Filters 70 and 80 are also shown as forming the ends of the hollow tube 60 thereby closing the tube to form chamber 64 for containing the gas sample.

Figure 5:
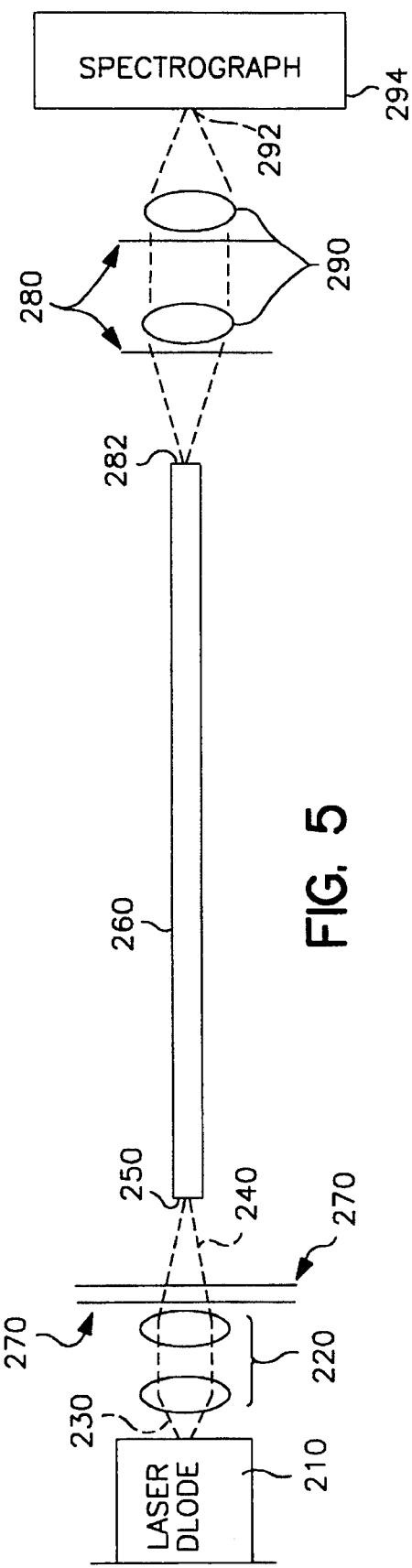
FIG. 5 is a schematic diagram illustrating a first alternative embodiment of the present invention having a conventional bulk optics coupling to a conventional spectrograph.

A first alternative embodiment of the invention is shown in FIG. 5. Light is produced by a diode laser 210. Beam shaping optics 220 collect the diode laser output 230, shape it appropriately, and direct the light 240 towards an aperture 250 in a proximate end of a hollow reflective tube 260. Before entering the hollow reflective tube 260 the light 230 passes through one or more dielectric filters 270 that allow only a narrow wavelength band centered on the laser line to pass through the filters 270 and enter the hollow reflective tube 260 through the aperture 250. Thus, the filtered output from the diode laser 210 passes through the optical aperture 250 at the proximate end of the hollow reflective tube 260 into the hollow reflective tube 260. In some embodiments, the aperture 250 and filter 270 are combined such that the filter 270 allows the laser light to enter the hollow reflective tube 260 and also serves to seal the aperture 250 of the hollow reflective tube 260 thus confining a sample gas within the hollow tube 260. The laser light then propagates through the hollow reflective tube 260 occasionally reflecting off the interior walls of the reflective hollow tube 260. As the laser light propagates through the gas sample contained within the reflective hollow tube 260, some of the laser light is Raman scattered from the sample gas thereby generating Raman scattered light which has wavelengths that are characteristic of the constituents of the sample gas. One or more laser line rejection filters 280 are positioned near a distal end 282 of the reflective hollow tube 260. Laser line rejection filters 280 are similar in construction to the band pass filters 270, but they pass the wavelengths of Raman scattered light comprising the Raman spectrum and reject the laser wavelength. Thus, the Raman scattered light passes through the filters while the laser light is reflected back through the reflective hollow tube 260. This reflected laser light again generates Raman scattering as it travels through the sample in a direction back towards the laser 210, effectively doubling the single pass power of the system. In the embodiment illustrated in FIG. 5, the light exiting the reflective hollow tube 260 is collected by beam shaping optics 290 and delivered to an entrance slit 292 of a spectrograph 294 for detection. The reflective hollow tube 260 is substantially the same as the reflective hollow tube 60 previously described.

Second, third and fourth alternative embodiments of the invention are shown in FIGS. 6a, 6b and 6c. As shown in FIGS. 6a, 6b and 6c a laser beam enters a reflective hollow tube 360 through an aperture 350 and one or more dielectric filters 370 that allow only a narrow wavelength band centered on the laser line to pass through the filter(s) 370 and propagate through the hollow reflective tube 360. In these embodiments, the aperture 350 and filter 370 are combined such that the filter 370 allows the laser light to enter the hollow reflective tube 360 and also serves to seal the aperture 350 of the hollow reflective tube 360 thus confining a sample gas within the hollow tube 360. The laser light then propagates through the hollow reflective tube 360 occasionally reflecting off the interior walls of the reflective hollow tube 360. As the laser light propagates through the gas sample contained within the reflective hollow tube 360, some of the laser light is Raman scattered from the sample gas thereby generating Raman scattered light which has wavelengths that are characteristic of the constituents of the sample gas. One or more laser line rejection filters 380 are positioned at a distal end of the reflective hollow tube 360. Laser line rejection filters 380 are similar in construction to the band pass filters 370, but they pass the wavelengths of Raman scattered light comprising the Raman spectrum and reject the laser wavelength. Thus, the Raman scattered light passes through the filters while the laser light is reflected back through the reflective hollow tube 360. This reflected laser light again generates Raman scattering as it travels through the sample in a direction back towards the laser entrance aperture 350, effectively doubling the single pass power of the system.

In the embodiment illustrated in FIG. 6a, the light exiting the reflective hollow tube 360 is delivered to an entrance slit of a spectrograph (not shown) by a fiber optic bundle 390 as previously described. The reflective hollow tube 360 is also substantially the same as the reflective hollow tube 60 previously described. In the embodiments shown in FIGS. 6b and 6c, a gradient index of refraction lens (GRIN lens) 392 is located adjacent the laser line rejection filter(s) 380 to improve the collection and delivery of the Raman scattered light from the gas sample to the optical fiber 390. Similarly, the embodiment shown in FIG. 6c, also includes a second GRIN lens 394 located adjacent the laser line band pass filter(s) 370 to improve the collection, delivery and transmission of the laser beam from the diode laser (not shown) into the reflective hollow tube 360.

Figure 7:
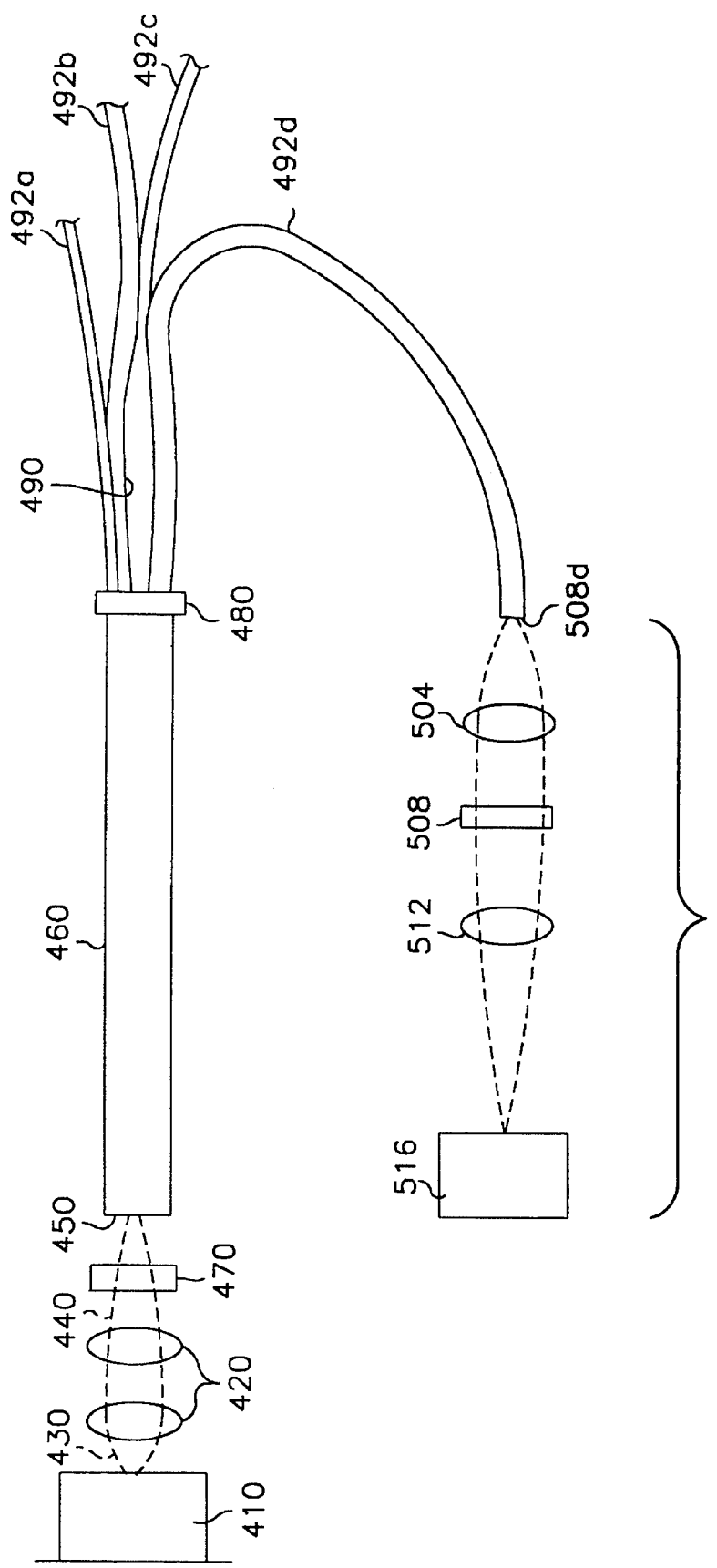
FIG. 7 is a schematic diagram illustrating a fifth alternative embodiment of the present invention having a multichannel detector system.

A fifth alternative embodiment of the invention is shown in FIG. 7. Similar to the embodiment shown in FIG. 1, light is produced by a diode laser 410. Beam shaping optics 420 collect the diode laser output 430, shape it appropriately, and direct the light 440 towards an aperture 450 in a proximate end of a hollow reflective tube 460. Before entering the hollow reflective tube 460 the light 440 passes through a dielectric filter 470 that allows only a narrow wavelength band centered on the laser line to pass through the filter 470 and enter the hollow reflective tube 460 through the aperture 450. Thus, the filtered output from the diode laser 410 passes through the optical aperture 450 at the proximate end of the hollow reflective tube 460 into the hollow reflective tube 460. In some embodiments, the aperture 450 and filter 470 are combined such that the filter 470 allows the laser light to enter the hollow reflective tube 460 and also serves to seal the aperture 450 of the hollow reflective tube 460 thus confining a sample gas within the hollow tube 460. The laser light then propagates through the hollow reflective tube 460 occasionally reflecting off the interior walls of the reflective hollow tube 460. As the laser light propagates through the gas sample contained within the reflective hollow tube 460, some of the laser light is Raman scattered from the sample gas thereby generating Raman scattered light which has wavelengths that are characteristic of the constituents of the sample gas. A laser line rejection filter 480 is positioned at a distal end of the reflective hollow tube 460. Laser line rejection filter 480 is similar in construction to the band pass filter 470, but it passes the wavelengths of Raman scattered light comprising the Raman spectrum and rejects the laser wavelength. Thus, the Raman scattered light passes through the filter while the laser light is reflected back through the reflective hollow tube 460. This reflected laser light again generates Raman scattering as it travels through the sample in a direction back towards the laser 410, effectively doubling the single pass power of the system.

In the embodiment illustrated in FIG. 7, the light exiting the reflective hollow tube 460 is collected by a fiber bundle 490. A proximate end of fiber bundle 490 is the same size as the reflective hollow tube exit aperture and can be polished so the filter coating 480 can be deposited directly onto the proximate end of the fiber bundle 490. Thus, the proximate end of fiber bundle 490 serves three functions: 1) it couples the light exiting from the hollow reflective tube 460 into the fiber 490; 2) it seals the distal end of the reflective hollow tube 460 thus confining the gas sample therein; and 3) it provides a substrate to support the filter 480. The fiber bundle 490 splits into multiple smaller fiber segments 492a, 492b, 492c, 492d, . . . , wherein each of the segments 492a, 492b, 492c, 492d, . . . is dedicated to directing a portion of the Raman scattered light from the gas sample in the reflective hollow tube 460 to a discrete detector channel 500a, 500b, 500c, 500d, . . . A detailed description of detector channel 500d will be understood to be representative of all of the detector channels 500a, 500b, 500c, . . . As shown in FIG. 7, detector channel 500d comprises a collection/collimation lens 504 which is f/# matched to the fiber 492d to optimally collect and collimate light exiting a distal end 508d of fiber segment 492d. A Raman line pass filter 508 receives the light from the lens 504 and passes only the Raman lines which that particular channel is designed to detect. Thus, each channel may be configured to detect a specific Raman line(s). After passing through the filter 508, the desired Raman line(s) are focused by a focusing lens 512 on a detector 516. The detector 516 may be any suitable light detector including but not limited to a photodiode or photomultiplier tube. Further details of multiple channel Raman detectors for gas analysis are described in U.S. Pat. No. 4,784,486 entitled "MULTI-CHANNEL MOLECULAR GAS ANALYSIS BY LASER-ACTIVATED RAMAN LIGHT SCATTERING", the entire contents of which are hereby incorporated herein by reference.

Figure 8:
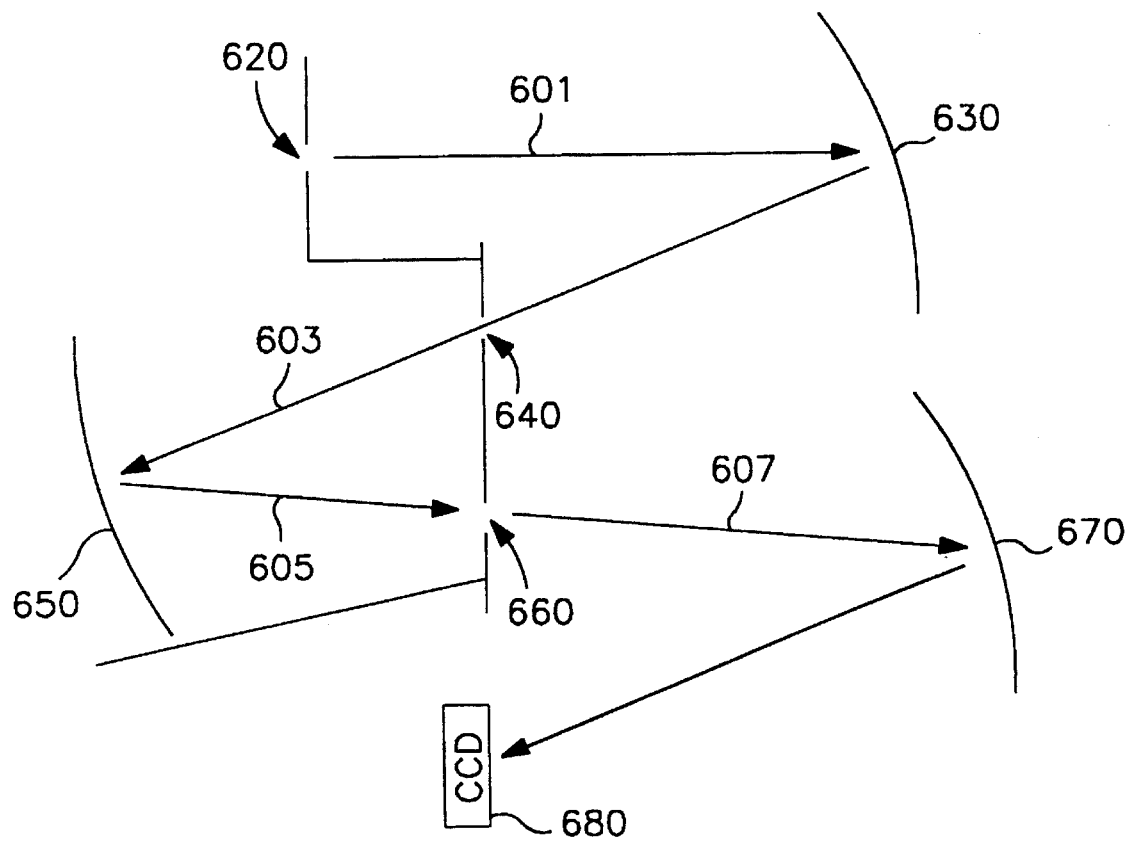
FIG. 8 is a schematic diagram illustrating two gratings used in a subtractive dispersion mode to replace a laser line rejection filter.

In alternate embodiments of the above described embodiments, the laser line rejection filters 80, 280, 380 and 480 may be replaced with two (2) gratings used in a subtractive dispersion mode as shown in FIG. 8. Light (601) exiting the reflective tube (not shown) passes through an entrance slit 620 and is incident on a first diffraction grating 630. Grating 620 produces a spectrally dispersed image of the entrance slit 620 at a first intermediate slit 640. Slit 640 is relatively wide, allowing the wavelengths of interest to pass through while blocking the laser line. This filtered light 603 continues on and is incident on another grating 650. Grating 650 acts as the reciprocal of the first grating 630, recombining the dispersed light and refocusing the filtered light 605 onto a second intermediate slit 660. Slit 660 is much narrower than the first intermediate slit 640. The filtered light 607 is then incident on a third grating 670 which acts to produce a spectrally dispersed image of the second intermediate slit 660 on a CCD 680. In summary, the first two gratings 630 and 650 act as a filter to remove the laser light, and the third grating 670 works in the conventional manner to disperse the wavelengths of the light contained in the beam 607 for detection by the CCD 680. Each of the previous embodiments which employ a spectrograph detector includes some type of dispersion element, for example, a grating, prism, etc.

The subtractive dispersion system shown in FIG. 8 is advantageous in that the laser light never passes through any filters or glass, thus fluorescence or Raman scattering from the filter coating or the glass is eliminated.

It will be understood that the apparatus and method of the present invention for a diode laser pumped Raman gas analysis system with reflective hollow tube gas cell may be employed with many different types of hollow reflective tubes, lasers, filters and detectors. Thus, there are numerous other embodiments of the present invention which will be obvious to one skilled in the art, including but not limited to changes in the dimensions of the reflective hollow tube, types of reflective materials utilized, and the location and type of filters and lenses. The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. An apparatus for the analysis of gases in a gas sample by Raman light scattering comprising:

a laser light source for producing and transmitting a laser beam of optical radiation along a longitudinal axis;

a gas sample cell to receive and hold the gas sample along said longitudinal axis in an interior region of said gas cell, wherein said gas sample cell is positioned to receive said laser beam of optical radiation from said laser light source via a first end of said gas sample cell, said gas sample cell further having a second end and a highly reflective interior surface suitable for reflecting said laser beam and Raman scattered light from the gas sample;

a laser line pass filter which transmits a narrow wavelength band of light centered on a laser line characteristic of said laser light source, wherein said laser line pass filter is positioned at said first end of said gas sample cell thereby transmitting that portion of said laser beam containing said characteristic laser line into said gas sample cell and rejecting substantially all other wavelengths comprising said laser beam, wherein said laser line pass filter further comprises:

a pass filter substrate having a first surface; and a pass filter coating formed on said first surface of said pass filter substrate, said laser line pass filter positioned immediately adjacent to said first end of said gas sample cell thereby closing said first end of said gas sample cell, said laser line pass filter positioned adjacent said first end of said gas sample cell such that said pass filter coating faces said interior region of said gas sample cell;

a laser line rejection filter which transmits substantially all wavelengths except the narrow wavelength band of light centered on the laser line characteristic of said laser light source, wherein said laser line rejection filter is positioned at said second end of said gas sample cell thereby transmitting light scattered by the gas sample at wavelengths different from the wavelength of the laser line characteristic of said laser light source out of said gas sample cell and reflecting said laser beam back through said sample cell, wherein said laser line rejection filter further comprises:

a rejection filter substrate having a first surface; and a rejection filter coating formed on said first surface of said rejection filter substrate, said laser line rejection filter positioned immediately adjacent to said second end of said gas sample cell thereby closing said second end of said gas sample cell, said laser line rejection filter positioned adjacent said second end of said gas sample cell such that said rejection filter coating faces said interior region of said gas sample cell; and a detector optically connected to said second end of said gas cell for receiving and detecting said light scattered from said gas sample and transmitted through said laser line rejection filter.

2. An apparatus as defined in claim 1 wherein said laser light source comprises a diode laser.

3. An apparatus as defined in claim 1 wherein said gas sample cell comprises an elongate hollow tube having a substantially uniform interior diameter and a length which is substantially greater than said interior diameter.

4. An apparatus as defined in claim 3 wherein said highly reflective interior surface of said gas sample cell comprises a metallic material.

5. An apparatus as defined in claim 4 wherein said highly reflective interior surface of said gas sample cell comprises gold.

6. An apparatus as defined in claim 1 wherein said pass filter coating is substantially non-hydrophilic.

7. An apparatus as defined in claim 6 wherein said pass filter coating comprises tantalum.

8. An apparatus as defined in claim 6 wherein said pass filter coating comprises silicon dioxide.

9. An apparatus as defined in claim 1 wherein said rejection filter coating is substantially non-hydrophilic.

10. An apparatus as defined in claim 9 wherein said rejection filter coating comprises tantalum.

11. An apparatus as defined in claim 9 wherein said rejection filter coating comprises silicon dioxide.

12. An apparatus as defined in claim 1 wherein said detector comprises a spectrograph.

13. An apparatus as defined in claim 1 further comprising a lens system positioned intermediate said laser light source and said gas sample cell, said lens collecting and focusing said laser beam of optical radiation from said laser light source and directing said laser beam of optical radiation into said first end of said gas sample cell.

14. An apparatus as defined in claim 13 wherein said lens system comprises a gradient index of refraction (GRIN) lens.

15. An apparatus as defined in claim 1 further comprising an optical fiber positioned intermediate said gas sample cell and said detector, said optical fiber transmitting said light scattered by the gas sample at wavelengths different from the wavelength of the laser line characteristic of said laser light source out of said gas sample cell into said detector.

16. An apparatus as defined in claim 1 further comprising a light guide positioned intermediate said gas sample cell and said detector, said optical fiber transmitting said light scattered by the gas sample at wavelengths different from the wavelength of the laser line characteristic of said laser light source out of said gas sample cell into said detector.

17. An apparatus as defined in claim 1 wherein said gas sample cell further comprises a gas input port and a gas output port.

18. An apparatus as defined in claim 1 further comprising:

an optical fiber positioned intermediate said gas sample cell and said detector, said optical fiber further comprising:

an input which receives, from said gas sample cell, said light scattered by the gas sample at wavelengths different from the wavelength of the laser line characteristic of said laser light source; and a plurality of outputs, wherein each output transmits a representative sample of said light scattered by the gas sample at wavelengths different from the wavelength of the laser line characteristic of said laser light source; and a plurality of detector channels, wherein each output of said plurality of outputs of said optical fiber is coupled to a discrete detector channel of said plurality of detector channels such that each discrete detector channel receives a signal which is representative of said light scattered by the gas sample at wavelengths different from the wavelength of the laser line characteristic of said laser light source.

19. An apparatus for the analysis of gases in a gas sample by Raman light scattering comprising:

a hollow tube for holding a sample of a gas to be analyzed, said hollow tube having a highly reflective interior tubular wall enclosing a bore forming a sample region, said bore having a length that is at least five times greater than its diameter, said bore having a longitudinal axis along its length;

a laser light source for producing and transmitting a laser beam of optical radiation into said hollow tube bore through a first end of said hollow tube such that a first portion of said beam of optical radiation propagates through said bore along said bore longitudinal axis and a second portion of said beam of optical radiation propagates through said bore by reflecting from said highly reflective interior tubular wall;

a laser line pass filter which transmits a narrow wavelength band of light centered on a laser line characteristic of said laser light source, wherein said laser line pass filter is positioned at said first end of said hollow tube thereby transmitting that portion of said laser beam containing said characteristic laser line into said bore and rejecting substantially all other wavelengths comprising said laser beam, wherein said laser line pass filter further comprises:
   a pass filter substrate having a first surface; and
   a pass filter coating formed on said first surface of said pass filter substrate, said laser line pass filter positioned immediately adjacent to said first end of said hollow tube thereby closing said first end of said hollow tube, said laser line pass filter positioned adjacent said first end of said hollow tube such that said pass filter coating faces said sample region of said hollow tube;

a laser line rejection filter which transmits substantially all wavelengths except the narrow wavelength band of light centered on the laser line characteristic of said laser light source, wherein said laser line rejection filter is positioned at a second end of said hollow tube thereby transmitting light scattered by the gas sample at wavelengths different from the wavelength of the laser line characteristic of said laser light source out of said hollow tube bore and reflecting said laser beam back through said hollow tube bore, wherein said laser line rejection filter further comprises:
   a rejection filter substrate having a first surface; and
   a rejection filter coating formed on said first surface of said rejection filter substrate, said laser line rejection filter positioned immediately adjacent to said second end of said hollow tube thereby closing said second end of said hollow tube, said laser line rejection filter positioned adjacent said second end of said hollow tube such that said rejection filter coating faces said sample region of said hollow tube; and a detector optically connected to said second end of said hollow tube for receiving and detecting said light scattered from said gas sample and transmitted through said laser line rejection filter.

20. An apparatus as defined in claim 19 wherein said laser light source comprises a diode laser.

21. An apparatus as defined in claim 19 wherein said highly reflective interior tubular wall of said hollow tube comprises a metallic material.

22. An apparatus as defined in claim 21 wherein said highly reflective interior tubular wall of said hollow tube comprises gold.

23. An apparatus as defined in claim 19 wherein said pass filter coating is substantially non-hydrophilic.

24. An apparatus as defined in claim 23 wherein said pass filter coating comprises tantalum.

25. An apparatus as defined in claim 23 wherein said pass filter coating comprises silicon dioxide.

26. An apparatus as defined in claim 19 wherein said rejection filter coating is substantially non-hydrophilic.

27. An apparatus as defined in claim 26 wherein said rejection filter coating comprises tantalum.

28. An apparatus as defined in claim 26 wherein said rejection filter coating comprises silicon dioxide.

29. An apparatus as defined in claim 19 wherein said detector comprises a spectrograph.

30. An apparatus as defined in claim 19 further comprising a lens positioned intermediate said laser light source and said hollow tube, said lens collecting and focusing said laser beam of optical radiation from said laser light source and directing said laser beam of optical radiation into said first end of said hollow tube.

31. An apparatus as defined in claim 30 wherein said lens comprises a gradient index of refraction (GRIN) lens.

32. An apparatus as defined in claim 19 further comprising an optical fiber positioned intermediate said hollow tube and said detector, said optical fiber transmitting said light scattered by the gas sample at wavelengths different from the wavelength of the laser line characteristic of said laser light source out of said hollow tube into said detector.

33. An apparatus as defined in claim 19 further comprising a light guide positioned intermediate said hollow tube and said detector, said optical fiber transmitting said light scattered by the gas sample at wavelengths different from the wavelength of the laser line characteristic of said laser light source out of said hollow tube into said detector.

34. An apparatus as defined in claim 19 wherein said hollow tube further comprises a gas input port and a gas output port.

35. An apparatus as defined in claims 19 further comprising:
   an optical fiber positioned intermediate said hollow tube and said detector, said optical fiber further comprising:
      an input which receives, from said hollow tube, said light scattered by the gas sample at wavelengths different from the wavelength of the laser line characteristic of said laser light source; and
      a plurality of outputs, wherein each output transmits a representative sample of said light scattered by the gas sample at wavelengths different from the wavelength of the laser line characteristic of said laser light source; and
   a plurality of separate detector channels, wherein each output of said plurality of outputs of said optical fiber is coupled to one of said separate detector channels such that each of said separate detector channels receives a signal which is representative of said light scattered by the gas sample at wavelengths different from the wavelength of the laser line characteristic of said laser light source.

36. A method of analyzing a gas sample comprising:
   providing a laser which produces a laser beam which propagates substantially along a longitudinal axis;
   directing said laser beam through a first end of a hollow tube having a longitudinal axis which is substantially aligned with said laser beam longitudinal axis wherein said hollow tube confines said gas sample inside a sample region surrounded by a highly reflective surface so that said laser beam propagates through said sample region such that a portion of said laser beam reflects from said highly reflective surface of said hollow tube while propagating through said sample region;
   providing a laser line pass filter in the path of said laser beam which transmits a specific wavelength characteristic of said laser wherein said laser line pass filter comprises a pass filter substrate having a first surface and a pass filter coating formed on said first surface of said pass filter substrate;
   positioning said laser line pass filter immediately adjacent to said first end of said hollow tube thereby closing said first end of said hollow tube, wherein said laser line pass filter is positioned adjacent said first end of said hollow tube such that said pass filter coating faces said sample region of said hollow tube;

providing a laser line rejection filter at a second end of said hollow tube which transmits a wavelength band including Raman lines characteristic of the constituents of said gas sample and reflects said specific wavelength characteristic of said laser wherein said laser line rejection filter comprises a rejection filter substrate having a first surface and a rejection filter coating formed on said first surface of said rejection filter substrate;

positioning said laser line rejection filter immediately adjacent to said second end of said hollow tube thereby closing said second end of said hollow tube, wherein said laser line rejection filter is positioned adjacent said second end of said hollow tube such that said rejection filter coating faces said sample region of said hollow tube; and detecting and analyzing said Raman lines which are characteristic of the constituents of said gas sample to identify said constituents.

37. An apparatus for the analysis of gases in a gas sample by Raman light scattering comprising:

a laser light source for producing and transmitting a laser beam of optical radiation along a longitudinal axis;

a gas sample cell to receive and hold the gas sample along said longitudinal axis in an interior region of said gas cell, wherein said gas sample cell is positioned to receive said laser beam of optical radiation from said laser light source via a first end of said gas sample cell, said gas sample cell further having a second end and a highly reflective interior surface suitable for reflecting said laser beam and Raman scattered light from the gas sample;

a laser line pass filter which transmits a narrow wavelength band of light centered on a laser line characteristic of said laser light source, wherein said laser line pass filter is positioned at said first end of said gas sample cell thereby transmitting that portion of said laser beam containing said characteristic laser line into said gas sample cell and rejecting substantially all other wavelengths comprising said laser beam, wherein said laser line pass filter further comprises:

a pass filter substrate having a first surface; and a pass filter coating formed on said first surface of said pass filter substrate, said laser line pass filter positioned immediately adjacent to said first end of said gas sample cell thereby closing said first end of said gas sample cell, said laser line pass filter positioned adjacent said first end of said gas sample cell such that said pass filter coating faces said interior region of said gas sample cell;

a subtractive dispersion laser line rejection filter which transmits a band of wavelengths including the Raman lines of interest but excluding the wavelength characteristic of said laser light source, wherein said subtractive dispersion laser line rejection filter is positioned at said second end of said gas sample cell thereby transmitting light scattered by the gas sample at wavelengths different from the wavelength of the laser line characteristic of said laser light source out of said gas sample cell; and a detector optically connected to said second end of said gas cell for receiving and detecting said light scattered from said gas sample and transmitted through said laser line rejection filter.

38. An apparatus as defined in claim 37 wherein said subtractive dispersion laser line rejection filter further comprises:

a first diffraction grating which receives light from said second end of said sample cell;

a first intermediate slit which receives light from said first diffraction grating and transmits the Raman scattered light and blocks the laser line;

a second diffraction grating which receives light from said first intermediate slit and recombines the dispersed wavelengths; and a second intermediate slit which receives light from said second diffraction grating and transmits the Raman scattered light.

39. An apparatus as defined in claim 38 wherein said second diffraction grating is the reciprocal of said first diffraction grating.

40. An apparatus as defined in claim 38 wherein said second intermediate slit is narrower than said first intermediate slit.

41. An apparatus for the analysis of gases in a gas sample by Raman light scattering comprising:

a laser light source for producing and transmitting a laser beam of optical radiation;

a gas sample cell to receive and hold the gas sample in an interior region of said gas sample cell, wherein said gas sample cell is positioned to receive said laser beam of optical radiation from said laser light source via a first end of said gas sample cell, said gas sample cell further having a second end;

a laser line pass filter which transmits a narrow wavelength band of light centered on a laser line characteristic of said laser light source, wherein said laser line pass filter is positioned at said first end of said gas sample cell thereby transmitting that portion of said laser beam containing said characteristic laser line into said gas sample cell and rejecting substantially all other wavelengths comprising said laser beam, wherein said laser line pass filter further comprises:

a pass filter substrate having a first surface; and a pass filter coating formed on said first surface of said pass filter substrate, said laser line pass filter positioned adjacent said first end of said gas sample cell such that said pass filter coating faces said interior region of said gas sample cell; and a detector optically connected to said second end of said gas sample cell for receiving and detecting light scattered from said gas sample.

42. An apparatus as defined in claim 41 further comprising a laser line rejection filter which transmits a wavelength band including Raman lines characteristic of the constituents of the gas sample and reflects a narrow wavelength band of light centered on the laser line characteristic of said laser light source, wherein said laser line rejection filter is positioned at said second end of said gas sample cell thereby transmitting light scattered by the gas sample at wavelengths contained in said wavelength band including Raman lines characteristic of the constituents of the gas sample out of said gas sample cell and reflecting said laser beam back through said gas sample cell, wherein said laser line rejection filter further comprises:

a rejection filter substrate having a first surface; and a rejection filter coating formed on said first surface of said rejection filter substrate, said laser line rejection filter positioned adjacent said second end of said gas sample cell such that said rejection filter coating faces said interior region of said gas sample cell.

43. An apparatus as defined in claim 42 wherein said laser line rejection filter further comprises an interference filter.

44. An apparatus as defined in claim 42 wherein said laser line pass filter further comprises an interference filter.

45. A method of analyzing a gas sample comprising:

providing a laser which produces a laser beam;

directing said laser beam through a first end of a gas cell wherein said gas cell confines said gas sample inside a sample region so that said laser beam propagates through said sample region and said gas sample;

providing a laser line pass filter in the path of said laser beam which transmits a specific wavelength which is characteristic of said laser wherein said laser line pass filter comprises a pass filter substrate having a first surface and a pass filter coating formed on said first surface of said pass filter substrate;

positioning said laser line pass filter adjacent to said first end of said gas cell such that said pass filter coating faces said sample region of said gas cell; and detecting and analyzing Raman lines which are characteristic of the constituents of said gas sample to identify said constituents.

46. A method as defined in claim 45 further comprising:

providing a laser line rejection filter at a second end of said gas cell which transmits a wavelength band including Raman lines which are characteristic of the constituents of said gas sample and reflects said specific wavelength which is characteristic of said laser wherein said laser line rejection filter comprises a rejection filter substrate having a first surface and a rejection filter coating formed on said first surface of said rejection filter substrate; and positioning said laser line rejection filter adjacent to said second end of said gas cell such that said rejection filter coating faces said sample region of said gas cell.

47. A method as defined in claim 46 further comprising:

positioning said laser line pass filter immediately adjacent to said first end of said gas cell thereby closing said first end of said gas cell; and positioning said laser line rejection filter immediately adjacent to said second end of said gas cell thereby closing said second end of said gas cell.

* * * * *